(12) United States Patent
Liu et al.

(10) Patent No.: US 10,961,519 B2
(45) Date of Patent: Mar. 30, 2021

(54) PHI29 DNA POLYMERASE MUTANT WITH INCREASED THERMOSTABILITY

(71) Applicant: MGI TECH CO., LTD., Shenzhen (CN)

(72) Inventors: Huanhuan Liu, Guangdong (CN); Yue Zheng, Guangdong (CN); Yujun Zhou, Guangdong (CN); Xi Zhang, Guangdong (CN); Zhougang Zhang, Guangdong (CN); Yuliang Dong, Guangdong (CN); Wenwei Zhang, Guangdong (CN); Chongjun Xu, Shenzhen (CN); Snezana Drmanac, Guangdong (CN)

(73) Assignee: MGI TECH CO., LTD., Shenzhen (CN)

( * ) Notice: Subject to any disclaimer, the term of this patent is extended or adjusted under 35 U.S.C. 154(b) by 0 days.

(21) Appl. No.: 16/657,713

(22) Filed: Oct. 18, 2019

(65) Prior Publication Data
US 2020/0115686 A1    Apr. 16, 2020

Related U.S. Application Data

(63) Continuation of application No. PCT/CN2017/082180, filed on Apr. 27, 2017.

(51) Int. Cl.
*C12N 9/12* (2006.01)
*C12N 7/00* (2006.01)

(52) U.S. Cl.
CPC ............. *C12N 9/1252* (2013.01); *C12N 7/00* (2013.01); *C12N 2795/00011* (2013.01); *C12Y 207/07007* (2013.01)

(58) Field of Classification Search
CPC .................................................... C12N 9/1252
See application file for complete search history.

(56) References Cited

U.S. PATENT DOCUMENTS

| | | |
|---|---|---|
| 2012/0034602 A1 | 2/2012 | Emig et al. |
| 2014/0094374 A1 | 4/2014 | Kamtekar et al. |
| 2014/0322759 A1 | 10/2014 | Skirgaila et al. |
| 2015/0218535 A1 | 8/2015 | Kamtekar et al. |
| 2016/0237412 A1 | 8/2016 | Kamtekar et al. |

OTHER PUBLICATIONS

International Search Report issued for PCT/CN2017/082180, dated Jan. 29, 2018.
Written Opinion of the International Searching Authority issued for PCT/CN2017/082180, dated Jan. 29, 2018.
Office Action issued for EP patent application 17907603.9 dated Nov. 6, 2020.
Bjornson, K., et al. "Phage phi29 DNA polymerase Y369R mutein" (2010).

*Primary Examiner* — Suzanne M Noakes
(74) *Attorney, Agent, or Firm* — Westman, Champlin & Koehler, P.A.; Z. Peter Sawicki; Amanda M. Prose

(57) ABSTRACT

Provided are a phi29 DNA polymerase mutant with increased thermo stability, a method for preparing the mutant, the use of the mutant, and a method for increasing the stability of the phi29 DNA polymerase.

6 Claims, 3 Drawing Sheets

Specification includes a Sequence Listing.

PHI29 DNA POLYMERASE MUTANT WITH INCREASED THERMOSTABILITY

CROSS-REFERENCE TO RELATED APPLICATIONS

This application is a continuation application of PCT Application No. PCT/CN2017/082180 filed on Apr. 27, 2017, the entire content of which is incorporated herein by reference.

FIELD

The present disclosure relates to the field of biotechnology, in particular to phi29 DNA polymerase mutant with increased thermo stability.

BACKGROUND

Phi29 DNA polymerase is a mesophilic DNA polymerase cloned from *Bacillus subtilis* phage phi29. It is a monomeric protein with a molecular weight of 66 kDa and has two domains, i.e., one domain located at the N-terminus having 3'-5' exonuclease activity, and the other domain located at the C-terminus having DNA-amplification and polymerization activity. Phi29 DNA polymerase has many properties, such as strong and continuous synthesis ability, strong proofreading activity, isothermal amplification, strand displacement, high coverage of amplification, unbiased amplification and the like. Therefore, it has been widely used in the fields of multiple displacement amplification (MDA), rolling cycle amplification (RCA), pair-end sequencing, single-cell sequencing and the like. However, the mesophilic nature of phi29 DNA polymerase causes a poor stability, resulting in a short storage period, thereby greatly increasing the cost of production, storage and transportation.

The existing solutions for overcoming the poor stability of phi29 DNA polymerase and disadvantages thereof are described as follows.

1) A 4° C. of refrigerator or chromatography cabinet is used to purify phi29 DNA polymerase, with deficiencies of high preparation cost and strict operation process.

2) The stock solution containing phi29 DNA polymerase is stored at a temperature of −20° C. or −80° C., with deficiencies such as a limited validity period at a low temperature and decreased activity with time.

3) Phi29 DNA polymerase in combination with reaction solution is stored in a kit, which will deteriorate its stability relative to separate storage of phi29 DNA polymerase, though being beneficial to customer use.

4) The stock solution containing phi29 DNA polymerase is optimized, such as addition of trehalose, bovine serum albumin (BSA) and the like. Addition of additive may be good for a low enzyme concentration, but cannot improve stability for a high enzyme concentration, thus the disadvantages of the current phi29 DNA polymerase cannot be solved fundamentally.

SUMMARY

The technical problem to be solved in the present disclosure is to improve the stability of phi29 DNA polymerase.

First, the present disclosure in embodiments provides a protein to solve the technical problem as described above.

The protein provided in embodiments of the present disclosure is any one of (1) to (17) as follows:

(1) a protein obtained by mutating glutamic acid at position 239 into tryptophan and keeping remaining amino acids unchanged relative to the amino acid sequence of phi29 DNA polymerase shown in SEQ ID NO: 2;

(2) a protein obtained by mutating glycine at position 217 into glutamic acid and keeping remaining amino acids unchanged relative to the amino acid sequence of phi29 DNA polymerase shown in SEQ ID NO: 2:

(3) a protein obtained by mutating tyrosine at position 224 into lysine and keeping remaining amino acids unchanged relative to the amino acid sequence of phi29 DNA polymerase shown in SEQ ID NO: 2;

(4) a protein obtained by mutating phenylalanine at position 526 into lysine and keeping remaining amino acids unchanged relative to the amino acid sequence of phi29 DNA polymerase shown in SEQ ID NO: 2;

(5) a protein obtained by mutating glutamine at position 171 into glutamic acid and keeping remaining amino acids unchanged relative to the amino acid sequence of phi29 DNA polymerase shown in SEQ ID NO: 2;

(6) a protein obtained by mutating valine at position 470 into lysine and keeping remaining amino acids unchanged relative to the amino acid sequence of phi29 DNA polymerase shown in SEQ ID NO: 2:

(7) a protein obtained by mutating glycine at position 217 into aspartic acid and keeping remaining amino acids unchanged relative to the amino acid sequence of phi29 DNA polymerase shown in SEQ ID NO: 2;

(8) a protein obtained by mutating leucine at position 216 into lysine and keeping remaining amino acids unchanged relative to the amino acid sequence of phi29 DNA polymerase shown in SEQ ID NO: 2;

(9) a protein obtained by mutating isoleucine at position 474 into lysine and keeping remaining amino acids unchanged relative to the amino acid sequence of phi29 DNA polymerase shown in SEQ ID NO: 2:

(10) a protein obtained by mutating threonine at position 140 into serine and keeping remaining amino acids unchanged relative to the amino acid sequence of phi29 DNA polymerase shown in SEQ ID NO: 2;

(11) a protein obtained by mutating glycine at position 197 into asparagine and keeping remaining amino acids unchanged relative to the amino acid sequence of phi29 DNA polymerase shown in SEQ ID NO: 2;

(12) a protein obtained by mutating threonine at position 140 into asparagine and keeping remaining amino acids unchanged relative to the amino acid sequence of phi29 DNA polymerase shown in SEQ ID NO: 2:

(13) a protein obtained by mutating serine at position 215 into aspartic acid and keeping remaining amino acids unchanged relative to the amino acid sequence of phi29 DNA polymerase shown in SEQ ID NO: 2;

(14) a protein obtained by mutating isoleucine at position 323 into asparagine and keeping remaining amino acids unchanged relative to the amino acid sequence of phi29 DNA polymerase shown in SEQ ID NO: 2;

(15) a protein obtained by mutating tyrosine at position 369 into arginine and keeping remaining amino acids unchanged relative to the amino acid sequence of phi29 DNA polymerase shown in SEQ ID NO: 2;

(16) a protein obtained by mutating valine at position 470 into lysine, isoleucine at position 474 into lysine and keeping remaining amino acids unchanged relative to the amino acid sequence of phi29 DNA polymerase shown in SEQ ID NO: 2; and

(17) a fusion protein obtained by ligating a tag at the N-terminus or/and the C-terminus of the protein being any one of (1) to (16).

According to the protein as described above, the phi29 DNA polymerase is a protein of a) or b), wherein a) is a protein consisting of the amino acid sequence shown in SEQ ID NO: 2 in the sequence listing; and b) is a protein derived from a) and has same function with a), formed by substituting, deleting and/or adding one or more amino acid residues of the amino acid sequence shown in SEQ ID NO: 2 in the sequence listing.

According to the protein as described above, the protein has increased stability compared to the phi29 DNA polymerase shown in SEQ ID NO: 2.

According to the protein as described above, the stability is thermal stability.

The protein having increased stability compared to the phi29 DNA polymerase shown in SEQ ID NO: 2 is specifically reflected by at least one feature of a1) to a3).

a1) The protein has a lower activity loss rate than that of phi29 DNA polymerase.

a2) The protein has a lower activity deterioration rate than that of phi29 DNA polymerase.

a3) The protein has a higher remaining activity ratio than that of phi29 DNA polymerase.

The present disclosure in embodiments also provides a nucleic acid molecule encoding the protein as described above so as to solve the technical problem.

The nucleic acid molecule as described above is a gene selected from 1) to 18).

1) is a DNA molecule having an encoding sequence which includes a mutation at position 715 from guanine (G) base to thymine (T) base, a mutation at position 716 from adenine (A) base to G base, and a mutation at position 717 from A base to G base relative to the DNA molecule shown in SEQ ID NO: 1 in the sequence listing.

2) is a DNA molecule having an encoding sequence which includes a mutation at position 650 from G base to A base and a mutation at position 651 from cytosine (C) base to A base relative to the DNA molecule shown in SEQ ID NO: 1 in the sequence listing.

3) is a DNA molecule having an encoding sequence which includes a mutation at position 670 from T base to A base and a mutation at position 672 from T base to A base relative to the DNA molecule shown in SEQ ID NO: 1 in the sequence listing.

4) is a DNA molecule having an encoding sequence which includes a mutation at position 1576 from T base to A base, a mutation at position 1577 from T base to A base and a mutation at position 1578 from C base to A base relative to the DNA molecule shown in SEQ ID NO: 1 in the sequence listing.

5) is a DNA molecule having an encoding sequence which includes a mutation at position 511 from C base to G base and a mutation at position 513 from G base to A base relative to the DNA molecule shown in SEQ ID NO: 1 in the sequence listing.

6) is a DNA molecule having an encoding sequence which includes a mutation at position 1408 from G base to A base, a mutation at position 1409 from T base to A base, and a mutation at position 1410 from G base to A base relative to the DNA molecule shown in SEQ ID NO: 1 in the sequence listing.

7) is a DNA molecule having an encoding sequence which includes a mutation at position 650 from G base to A base and a mutation at position 651 from C base to T base relative to the DNA molecule shown in SEQ ID NO: 1 in the sequence listing.

8) is a DNA molecule having an encoding sequence which includes a mutation at position 646 from C base to A base, a mutation at position 647 from T base to A base, and a mutation at position 648 from G base to A base relative to the DNA molecule shown in SEQ ID NO: 1 in the sequence listing.

9) is a DNA molecule having an encoding sequence which includes a mutation at position 1421 from T base to A base and a mutation at position 1422 from T base to A base relative to the DNA molecule shown in SEQ ID NO: 1 in the sequence listing.

10) is a DNA molecule having an encoding sequence which includes a mutation at position 419 from C base to 0 base relative to the DNA molecule shown in SEQ ID NO: 1 in the sequence listing.

11) is a DNA molecule having an encoding sequence which includes a mutation at position 589 from G base to A base and a mutation at position 590 from G base to A base relative to the DNA molecule shown in SEQ ID NO: 1 in the sequence listing.

12) is a DNA molecule having an encoding sequence which includes a mutation at position 419 from C base to A base relative to the DNA molecule shown in SEQ ID NO: 1 in the sequence listing.

13) is a DNA molecule having an encoding sequence which includes a mutation at position 643 from A base to G base, a mutation at position 644 from G base to A base and a mutation at position 645 from C base to T base relative to the DNA molecule shown in SEQ ID NO: 1 in the sequence listing.

14) is a DNA molecule having an encoding sequence which includes a mutation at position 968 from T base to A base relative to the DNA molecule shown in SEQ ID NO: 1 in the sequence listing.

15) is a DNA molecule having an encoding sequence which includes a mutation at position 1105 from T base to C base and a mutation at position 1106 from A base to G base relative to the DNA molecule shown in SEQ ID NO: 1 in the sequence listing.

16) is a DNA molecule having an encoding sequence which includes a mutation at position 1408 from G base to A base, a mutation at position 1409 from T base to A base, a mutation at position 1410 from G base to A base, a mutation at position 1421 from T base to A base and a mutation at position 1422 from T base to A base relative to the DNA molecule shown in SEQ ID NO: 1 in the sequence listing.

17) is a DNA molecule which hybridizes with the DNA molecule as defined in 1) to 16) under stringency conditions and encodes the protein as described above.

18) is a DNA molecule having 90% or more sequence homology with the DNA molecule as defined in 1) to 6) and encoding the protein as described above.

The present disclosure in embodiments further provides a biomaterial being any one of a1) to a4) so as to solve the technical problem.

a1) is an expression cassette comprising the nucleic acid molecule as described above.

a2) is a recombinant vector comprising the nucleic acid molecule as described above.

a3) is a recombinant bacterium comprising the nucleic acid molecule as described above.

a4) is a transgenic cell line comprising the nucleic acid molecule as described above.

The recombinant vector may be a recombinant plasmid obtained by inserting the nucleic acid molecule as described above into an expression vector or a cloning vector. Specifically, the expression vector may be vector pET28a proposed in examples.

Specifically, the recombinant vector may be recombinant vector T140S, recombinant vector T140N, recombinant vector QI71E, recombinant vector G197N, recombinant vector S215D, recombinant vector L216K, recombinant vector 0217D, recombinant vector 0217E, recombinant vector Y224K, recombinant vector E239W, recombinant vector Y369R, recombinant vector I323N, recombinant vector V470K, recombinant vector 1474K, recombinant vector F526K or recombinant vector V470K-1474K proposed in examples.

The recombinant bacterium is a bacterium obtained by inserting the recombinant vector into an original bacterium.

The original bacterium can be *Escherichia coli*.

Specifically, the *Escherichia coli* can be *Escherichia coli* BL21 (DE3).

The transgenic cell line can be obtained by transforming the recombinant vector into recipient cells. The transgenic cell line is a non-plant propagative material.

The present disclosure in embodiments further provides use of the protein as described above, the nucleic acid molecule as described above, or the biomaterial as described above so as to solve the technical problem.

The present disclosure in embodiments provides use of the protein as described above, the nucleic acid molecule as described above or the biomaterial as described above in the preparation of phi29 DNA polymerase.

The present disclosure in embodiments also provides use of the protein as described above, the nucleic acid molecule as described above or the biomaterial as described above in PCR amplification.

The present disclosure in embodiments also provides use of the protein as described above, the nucleic acid molecule as described above or the biomaterial as described above in sequencing.

The present disclosure in embodiments also provides use of the protein as described above, the nucleic acid molecule as described above or the biomaterial as described above in the preparation of a sequencing product.

According to the use as described above, the sequencing product is a kit.

The present disclosure in embodiments further provides a method for improving stability of phi29 DNA polymerase so as to solve the technical problem.

The method for improving stability of phi29 DNA polymerase according to the present disclosure comprises mutating one or more amino acids at positions 140, 171, 197, 215, 216, 217, 224, 239, 369, 323, 470, 474 and 526 of the amino acid sequence of phi29 DNA polymerase shown in SEQ ID NO: 2.

According to the method as described above, the stability is thermal stability.

BRIEF DESCRIPTION OF THE DRAWINGS

FIG. 2A shows the comparison of enzyme activity of the pure wild-type phi29 DNA polymerase and phi29 DNA polymerase mutants V470K and 1474K under different treatment conditions, and FIG. 2B shows the comparison of remaining activity ratio of the pure wild-type phi29 DNA polymerase and phi29 DNA polymerase mutants V470K and 1474K under different treatment conditions.

FIG. 3A shows the comparison of enzyme activity of the pure wild-type phi29 DNA polymerase and phi29 DNA polymerase mutant V470K-1474K under different treatment conditions, and FIG. 3B shows the comparison of remaining activity ratio of the pure wild-type phi29 DNA polymerase and phi29 DNA polymerase mutant V470K-474K under different treatment conditions.

DETAILED DESCRIPTION

Figure 1:
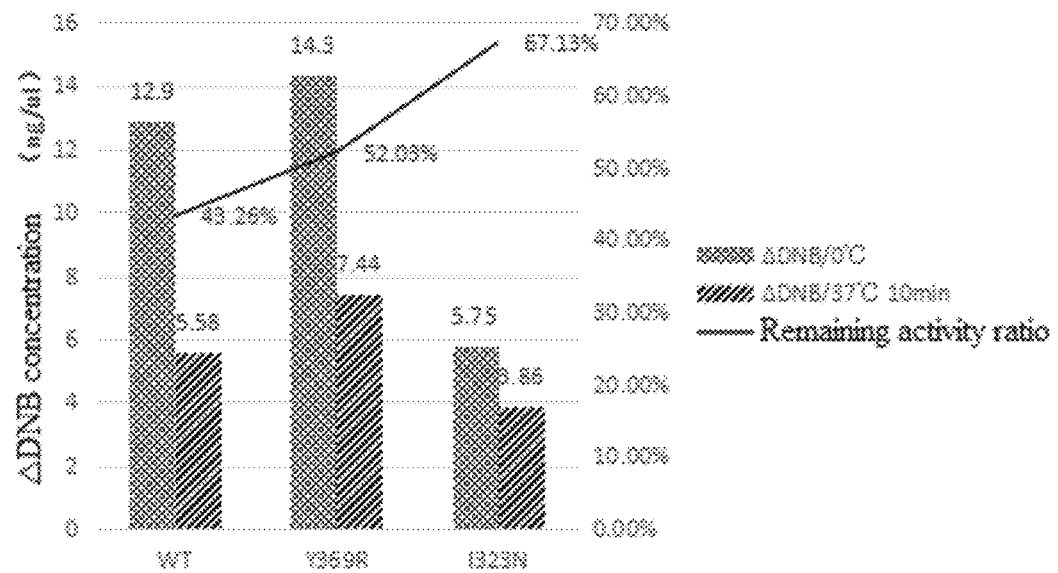
FIG. 1 shows the DNA Nano ball (DNB) concentration produced in the presence of crude wild-type phi29 DNA polymerase and phi29 DNA polymerase mutant Y369R and remaining activity ratio thereof in the stability assay.

The experimental methods used in the examples as below are all conventional methods unless otherwise specified.

The materials, reagents and the like used in the examples are all commercially available unless otherwise specified.

The quantitative assays in the examples are all conducted in triplicate, and the results were averaged.

Lysis mixture used in examples (500 μL per tube) is of a formulation comprising 440 μL lysate (20 mM Tris-HCl, TB0194-500G BBI), 500 mM NaCl (Analytial Reagent from Guangzhou Chemicalreagent Co., Lmt.), 0.5% Tween-20 (TB0560-500ML, BBI), 5% Glycerol (G5516-IL, SIGMA), 50 μL 10 mg/ml lysozyme (1 mg/ml of final concentration, A610308-0005, BB) and 10 μL 0.1M Phenylmethanesulfonyl fluoride (PMSF, 10 mM of final concentration, 16A6063-25G BBI). The lysis mixture is used right after it was ready.

Reaction Buffer 10×phi29 used in examples (1 L) is of a formulation comprising 60.57 g Tris (TB0194-500G BBI), 6.17 g Dithiothreitol (DTT A620058-0100, BBI), 13.2 g $(NH_4)_2SO_4$ (A610060-0500, BBI), 9.5 g $MgCl_2.6H_2O$ (M0250-500, SIGMA) and 25 mM dNTP Solution Mix (1 ml, ENZYMATICS), pH 7.5.

141 RCA Primer used in examples is TCTAA-GACCGCITGCCTCCGAC. (SEQ ID NO: 3)

141 Ad ssDNA used in examples is made by BGI, which is a single-stranded loop library within a certain length range and has no fixed sequence.

Example 1 Obtaining Phi29 DNA Polymerase Mutants with a Single Mutation 1.1 Construction of expression vectors A recombinant vector WT was obtained by replacing the sequence between the BamHI and NdeI restriction sites of the pET28a vector (from Novagen) with the encoding gene of phi29 DNA polymerase shown in SEQ ID NO: 1, which can express a phi29 DNA polymerase having an amino acid sequence shown in SEQ ID NO: 2, i.e. the wide-type phi29 DNA polymerase.

A recombinant vector T140S was obtained by mutating C base at position 419 into G base relative to the encoding gene of phi29 DNA polymerase in the recombinant vector WT, which can express a phi29 DNA polymerase mutant having an amino acid sequence which includes a mutation at position 140 from threonine (Thr, T) to serine (Ser, S) and unchanged remaining amino acids compared to the amino acid sequence shown in SEQ ID NO: 2.

A recombinant vector T140N was obtained by mutating C base at position 419 into A base relative to the encoding gene of phi29 DNA polymerase in the recombinant vector WT, which can express a phi29 DNA polymerase mutant having an amino acid sequence which includes a mutation at position 140 from threonine (Thr, T) to asparagine (Asn, N) and unchanged remaining amino acids compared to the amino acid sequence shown in SEQ ID NO: 2.

A recombinant vector Q171E was obtained by mutating C base at position 511 into G base and G base at position 513 into A base relative to the encoding gene of phi29 DNA polymerase in the recombinant vector WT, which can express a phi29 DNA polymerase mutant having an amino acid sequence which includes a mutation at position 171 from glutamine (Gln, Q) to glutamic acid (Glu, E) and unchanged remaining amino acids compared to the amino acid sequence shown in SEQ ID NO: 2.

A recombinant vector G197N was obtained by mutating G base at position 589 into A base and G base at position 590 into A base relative to the encoding gene of phi29 DNA polymerase in the recombinant vector WT, which can express a phi29 DNA polymerase mutant having an amino acid sequence which includes a mutation at position 197 from glycine (Gly, G) to asparagine (Asn, N) and unchanged remaining amino acids compared to the amino acid sequence shown in SEQ ID NO: 2.

A recombinant vector S215D was obtained by mutating A base at position 643 into G base, 0 base at position 644 into A base, and C base at position 645 into T base relative to the encoding gene of phi29 DNA polymerase in the recombinant vector WT, which can express a phi29 DNA polymerase mutant having an amino acid sequence which includes a mutation at position 215 from serine (Ser. S) to aspartic acid (Asp, D) and unchanged remaining amino acids compared to the amino acid sequence shown in SEQ ID NO: 2.

A recombinant vector L216K was obtained by mutating C base at position 646 into A base, T base at position 647 into A base, and G base at position 648 into A base relative to the encoding gene of phi29 DNA polymerase in the recombinant vector WT which can express a phi29 DNA polymerase mutant having an amino acid sequence which includes a mutation at position 216 from leucine (Leu, L) to lysine (Lys, K) and unchanged remaining amino acids compared to the amino acid sequence shown in SEQ ID NO: 2.

A recombinant vector G217D was obtained by mutating G base at position 650 into A base and C base at position 651 into T base relative to the encoding gene of phi29 DNA polymerase in the recombinant vector WT, which can express a phi29 DNA polymerase mutant having an amino acid sequence which includes a mutation at position 217 from glycine (Gly, G) to aspartic acid (Asp, D) and unchanged remaining amino acids compared to the amino acid sequence shown in SEQ ID NO: 2.

A recombinant vector G217E was obtained by mutating G base at position 650 into A base and C base at position 651 into A base relative to the encoding gene of phi29 DNA polymerase in the recombinant vector WT, which can express a phi29 DNA polymerase mutant having an amino acid sequence which includes a mutation at position 217 from glycine (Gly, G) to glutamic acid (Glu, E) and unchanged remaining amino acids compared to the amino acid sequence shown in SEQ ID NO: 2.

A recombinant vector Y224K was obtained by mutating T base at position 670 into A base and T base at position 672 into A base relative to the encoding gene of phi29 DNA polymerase in the recombinant vector WT, which can express a phi29 DNA polymerase mutant having an amino acid sequence which includes a mutation at position 224 from tyrosine (Tyr, Y) to lysine (Lys, K) and unchanged remaining amino acids compared to the amino acid sequence shown in SEQ ID NO: 2.

A recombinant vector E239W was obtained by mutating G base at position 715 into T base, A base at position 716 into (base and A base at position 717 into 0 base relative to the encoding gene of phi29 DNA polymerase in the recombinant vector WT which can express a phi29 DNA polymerase mutant having an amino acid sequence which includes a mutation at position 239 from glutamic acid (Glu, E) to tryptophan (Trp W) and unchanged remaining amino acids compared to the amino acid sequence shown in SEQ ID NO: 2.

A recombinant vector Y369R was obtained by mutating T base at position 1105 into C base and A base at position 1106 into G base relative to the encoding gene of phi29 DNA polymerase in the recombinant vector WT, which can express a phi29 DNA polymerase mutant having an amino acid sequence which includes a mutation at position 369 from tyrosine (Tyr, Y) to arginine (Arg, R) and unchanged remaining amino acids compared to the amino acid sequence shown in SEQ ID NO: 2.

A recombinant vector 1323N was obtained by mutating T base at position 968 into A base relative to the encoding gene of phi29 DNA polymerase in the recombinant vector WT, which can express a phi29 DNA polymerase mutant having an amino acid sequence which includes a mutation at position 323 from isoleucine (Ile, I) to asparagine (Asn, N) and unchanged remaining amino acids compared to the amino acid sequence shown in SEQ ID NO: 2.

A recombinant vector V470K was obtained by mutating G base at position 1408 into A base, T base at position 1409 into A base and G base at position 1410 into A base relative to the encoding gene of phi29 DNA polymerase in the recombinant vector WI, which can express a phi29 DNA polymerase mutant having an amino acid sequence which includes a mutation at position 470 from valine (Val. V) to lysine (Lys. K) and unchanged remaining amino acids compared to the amino acid sequence shown in SEQ ID NO: 2.

A recombinant vector 1474K was obtained by mutating T base at position 1421 into A base and T base at position 1422 into A base relative to the encoding gene of phi29 DNA polymerase in the recombinant vector WT, which can express a phi29 DNA polymerase mutant having an amino acid sequence which includes a mutation at position 474 from isoleucine (Ile, I) to lysine (Lys, K) and unchanged remaining amino acids compared to the amino acid sequence shown in SEQ ID NO: 2.

A recombinant vector F526K was obtained by mutating T base at position 1576 into A base, T base at position 1577 into A base and C base at position 1578 into A base relative to the encoding gene of phi29 DNA polymerase in the recombinant vector WT, which can express a phi29 DNA polymerase mutant having an amino acid sequence which includes a mutation at position 526 from phenylalanine (Phe, F) to lysine (Lys, K) and unchanged remaining amino acids compared to the amino acid sequence shown in SEQ ID NO: 2.

1.2 Construction and Induced Expression of Recombinant Bacteria 1.2.1 Construction of Recombinant Bacteria Recombinant bacteria were obtained by transforming the recombinant vector WT, the recombinant vector T140S, the recombinant vector T140N, the recombinant vector QI71E, the recombinant vector G197N, the recombinant vector S215D, the recombinant vector L216K, the recombinant vector G217D, the recombinant vector G217E, the recombinant vector Y224K, the recombinant vector E239W, the recombinant vector Y369R, the recombinant vector I323N, the recombinant vector V470K, the recombinant vector I474K and the recombinant vector F526K constructed in 1.1 into *Escherichia coli* BL21 (DE3) (TIANGEN, CB105-02) respectively.

1.2.2 Induced Expression of Recombinant Bacteria

The recombinant bacteria obtained in 1.2.1 were individually induced to express corresponding phi29 DNA polymerase, and wild-type phi29 DNA polymerase (WT), phi29 DNA polymerase mutant T140S, phi29 DNA polymerase mutant T40N, phi29 DNA polymerase mutant Q171E, phi29 DNA polymerase mutation 0197N, phi29 DNA polymerase mutant S215D, phi29 DNA polymerase mutant L216K, phi29 DNA polymerase mutant G217D, phi29 DNA polymerase mutant 0217E, phi29 DNA polymerase mutant Y224K, phi29 DNA polymerase mutant E239W, phi29 DNA polymerase mutant Y369R, phi29 DNA polymerase mutant I323N, phi29 DNA polymerase mutant V470K, phi29 DNA polymerase mutant 1474K and phi29 DNA polymerase mutant F526K were respectively obtained. The induction was conducted according to the following specific steps.

Step 1. Activation of Culture

The glycerol stocks of *Escherichia coli* BL21 (DE3) transformed with wild-type phi29 DNA polymerase or phi29 DNA polymerase mutant were seeded into 3 ml of liquid LB medium containing kanamycin and cultured overnight.

Step 2. Transfer of Bacterial Solution

The bacterial solution obtained in step 1 was transferred into 2 L of liquid LB medium containing kanamycin at a volume ratio of 1:100 and cultured in a shaker at 37° C. for 3 hours.

Step 3. Induction of Expression

Isopropyl-beta-D-thiogalactopyranoside (IPTG) with a final concentration of 0.5 mM was added for inducing expression and the mixture was cultured in a shake at 30° C. for another 2 to 2.5 hours.

Step 4. Collection of Bacterial Pellet

The bacterial solution was centrifuged at 12.00 rpm for 1 minute and bacterial pellets were collected.

1.3 Stability Assay of Phi29 DNA Polymerase 1.3.1 Treatment of Bacterial Pellet

The bacterial pellets obtained in step 1.2.2 were mixed with the lysis mixture, lysed in a water bath at 30° C. for 10 minutes and centrifuged at 12000 rpm and 4° C. for 10 minutes, and the supernatant was collected as crude phi29 DNA polymerase which was placed on ice for use.

1.3.2 Detection of Crude Enzyme for Stability Via RCA Reaction

20 µL of crude enzyme solution of wild-type phi29 DNA polymerase (WT) or individual phi29 DNA polymerase mutants obtained in step 1.3.1 was subjected to heat treatment at 37° C. for 10 minutes, 1 µL of the crude enzyme solution before and after heat treatment was respectively added into 40.4 µL of denatured RCA reaction system (refer to Table 1), and subjected to RCA reaction at 30° C. for 30 minutes. After that, 2.5 µL of 0.5M EDTA as a stop solution (AM9261, INVITROGEN) was added to terminate the RCA reaction. Besides, a group of denatured RCA reaction system containing the heat-treated crude enzyme was added with the stop solution before the initiation of RCA reaction, which was used as a negative control group. All samples obtained were detected by using Qubit ssDNA Assay Kit (Q10212, INVITROGEN) for DNA Nano ball (DNB) concentration produced.

The remaining activity ratio of wild-type phi29 DNA polymerase or individual phi29 polymerase mutants was calculated according to the following formula:

Remaining activity ratio=$(N_2\ N_0)/(N_1\ N_0)*100\%$ in which, $N_0$ indicates the DNB concentration of negative control, $N_1$ indicates the DNB concentration produced in the presence of crude enzyme (without heat treatment) after the RCA reaction, and $N_2$ indicates the DNB concentration produced in the presence of heat-treated crude enzyme after the RCA reaction.

TABLE 1

| RCA reaction system | | |
|---|---|---|
| Reagent | Volume (×1) | Volume (×10) |
| 10×phi29 Reaction Buffer | 4.0 µL | 40 µL |
| 5 µM 141 RCA Primer | 0.2 µL | 2.0 µL |
| 25 mM dNTPs Mix | 1.0 µL | 10 µL |
| 141Ad ssDNA | 3 ng | 30 ng |
| H₂O | 35.2-sample) µL | (35.2-sample) ×10 µL |

The detection results are shown in Table 2 and FIG. 1, which indicate that the wild-type phi29 DNA polymerase (W) and the phi29 DNA polymerase mutants Y369R and 1323N respectively have a remaining activity ratio of 43.26%, 52.03% and 67.13%, showing the remaining activity ratio of the phi29 DNA polymerase mutants Y369R and I323N has increased by 9% and 24% respectively compared to the wild-type phi29 DNA polymerase. The results demonstrate that the phi29 DNA polymerase mutants have increased stability compared to the wild-type phi29 DNA polymerase.

TABLE 2

Detection results of crude phi29 DNA polymerase mutants Y369R and I323N for stability

| Polymerase type | Heat treatment temperature | DNB concentration after RCA reaction (ng/µL) | | Remaining activity ratio |
|---|---|---|---|---|
| | | 0 min | 10 min | |
| WT | 37° C. | 12.9 | 5.58 | 43.26% |
| Y369R | 37° C. | 14.3 | 7.44 | 52.03% |
| I323N | 37° C. | 5.75 | 3.86 | 67.13% |

Other heat-treated crude phi29 DNA polymerase mutants also have an increased remaining activity ratio compared to the wild-type phi29 DNA polymerase, for example, the phi29 DNA polymerase mutants T140S, T140N, QI71E, G197N, S215D, L216K, G217E, G217D, Y224K, E239W, V470K. V474K and F526K respectively have a remaining activity ratio of 52%, 73%, 51%, 47.7%, 63%, 47.27%, 65.24%, 59%, 74.76%, 69.83%, 63.98%, 85.54% and 60.5%, etc.

1.3.3 Detection of Pure Enzyme for Stability Via RCA Reaction

1 L of bacterial pellets containing wild-type phi29 DNA polymerase (WT) or individual phi29 DNA polymerase mutants subjected to IPTG-induction and obtained in 1.2.2 were respectively purified through the affinity chromatography and ion exchange by using the ÄKTA pure system, thereby obtaining pure wild-type phi29 DNA polymerase (WT) and individual phi29 DNA polymerase mutants respectively, 20 μL of obtained pure enzyme solution was individually subjected to heat treatment at −20° C., 34° C. and 37° C. respectively for 10 minutes, 1 μL of the pure enzyme solution after heat treatment at different temperatures was respectively added into 80.8 μL of denatured RCA reaction system (with twice volume of that listed in Table 1) and subjected to RCA reaction at 30° C. for 30 minutes. After that, 5 μL of 0.5M EDTA as a stop solution was added to terminate the RCA reaction. All samples obtained were detected by using Qubit ssDNA Assay Kit (Q10212, INVITROGEN) for DNB concentration produced in the presence of wild-type phi29 DNA polymerase or individual phi29 DNA polymerase mutants, and the remaining activity ratio of enzyme was calculated.

Figure 2A:
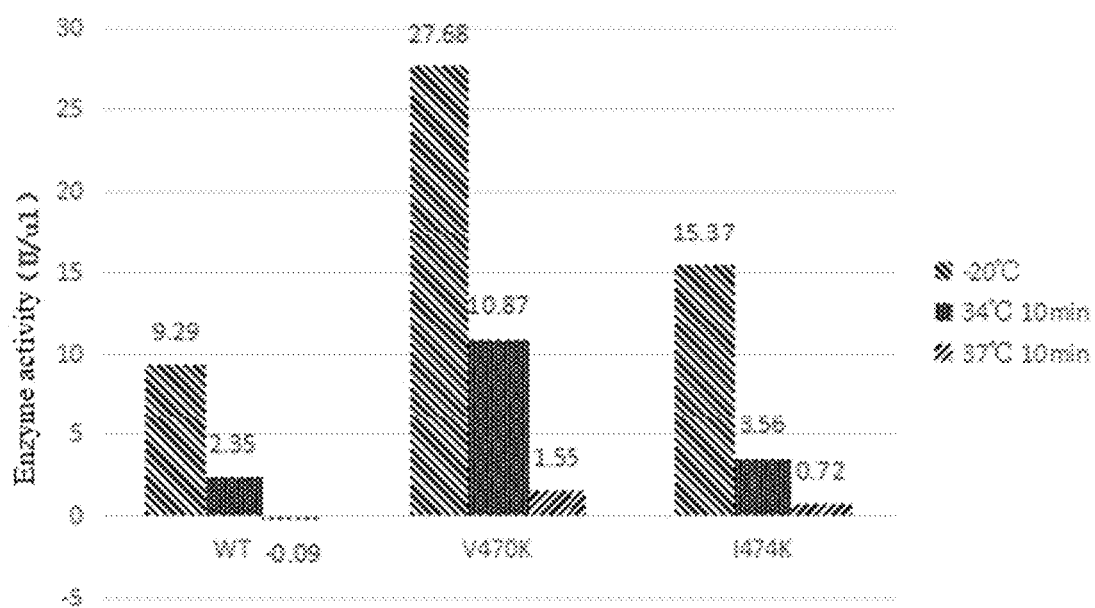
FIG. 2A and FIG. 2B show the detection results of pure wild-type phi29 DNA polymerase and phi29 DNA polymerase mutants V470K and I474K for stability, where
Figure 2B:
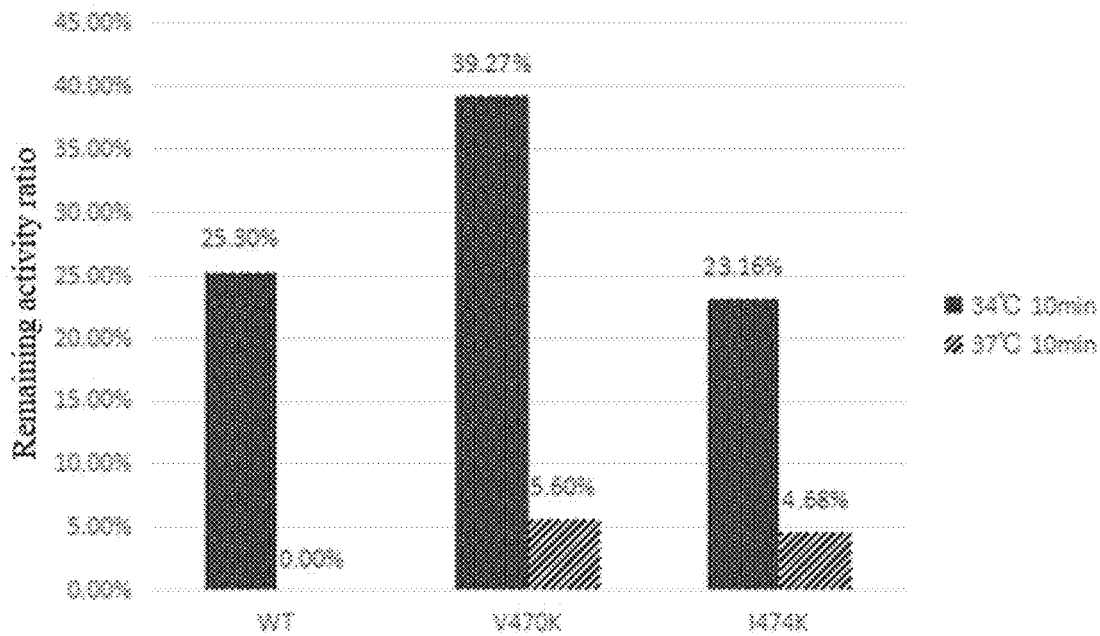

The results are shown in FIG. 2A and FIG. 2B and Table 3. After treatment at 34° C. and 37° C. for 10 minutes, the wild-type phi29 DNA polymerase respectively has a remaining activity ratio of 25.3% and 0%, the phi29 DNA polymerase mutant V470K respectively has a remaining activity ratio of 39.27% and 5.6%, and the phi29 DNA polymerase mutant I474K respectively has a remaining activity ratio of 23.16% and 4.68%. It can be seen that the phi29 DNA polymerase mutants V470K and I474K each have increased thermal stability compared to the wild-type of phi29 DNA polymerase. In addition, the commercial enzyme Enzymatics after treatment at 37° for 10 minutes and 5 minutes has a remaining activity ratio of 5.02% and 17.06% respectively, which may slightly higher than some mutant with single-point mutation, but has no significant advantages.

TABLE 3

Detection results of pure phi29 DNA polymerase mutants V470K and I474K and commercial enzyme *Enzymatics* for stability

| Polymerase type | Heat treatment temperature | Heat treatment time | Enzyme activity (U/μL) | Remaining activity ratio |
|---|---|---|---|---|
| WT | −20° C. | N/A | 9.29 | N/A |
| | 34° C. | 10 min | 2.35 | 25.30% |
| | 37° C. | 10 min | −0.09 | 0.00% |
| V470K | −20° C. | N/A | 27.68 | N/A |
| | 34° C. | 10 min | 10.87 | 39.27% |
| | 37° C. | 10 min | 1.55 | 5.60% |
| I474K | −20° C. | N/A | 15.37 | N/A |
| | 34° C. | 10 min | 3.56 | 23.16% |
| | 37° C. | 10 min | 0.72 | 4.68% |
| Enzymatics | −20° C. | N/A | 88.85 | N/A |
| | 37° C. | 5 min | 15.16 | 17.06% |
| | | 10 min | 4.46 | 5.02% |

Other pure phi29 DNA polymerase mutants after treatment at 37° C. for 10 minutes also has an increased remaining activity ratio compared to the wild-type phi29 DNA polymerase, for example, the phi29 DNA polymerase mutants T140S, T140N, Q171E, G197N, S2151D, L216K, G217E, E239W, G217D, Y224K, F526K, L323N and Y369R respectively have a remaining activity ratio of 3.81%, 1.51%, 6.06%, 3.18%, 1.40%, 5.04%, 14.76%, 15.27%, 5.21%, 12.84%, 10%, 1.25% and 1.1% etc.

Example 2 Obtaining Phi29 DNA Polymerase Mutant with Multiple Mutation 2.1 Construction of Recombinant Vector A recombinant vector V470K-474K was obtained by mutating G base at position 1408 into A base, T base at position 1409 into A base, G base at position 1410 into A base. T base at position 1421 into A base and T base at position 1422 into A base relative to the encoding gene of phi29 DNA polymerase in the recombinant vector WT, which can express phi29 DNA polymerase mutant V470K-1474K having an amino acid sequence which includes a mutation at position 470 from valine (Val, V) to lysine (Lys, K), a mutation at position 474 from isoleucine (Ile, I) to lysine (Lys. K) and unchanged remaining amino acids compared to the amino acid sequence shown in SEQ ID NO: 2.

2.2 Construction and Induced Expression of Recombinant Bacteria

Recombinant bacteria were obtained by transforming the recombinant vector V470K-1474K constructed in 2.1 into *Escherichia coli* BL21 (DE3), which was then induced to express phi29 DNA polymerase mutant V470K-474K according to the method in 1.2.2, and bacterial pellts were obtained.

2.3 Detection of Pure Enzyme for Stability

The bacterial pellets subjected to induction and obtained in 2.2 were purified according to the method in 1.3, thus obtaining pure phi29 DNA polymerase mutant V470K-474K. 20 μL of obtained pure phi29 DNA polymerase mutant V470K-1474K was subjected to heat treatment at 37° C. for 5 minutes and 10 minutes respectively, 1 μL of the pure enzyme solution after heat treatment at different treatment times was respectively added into 40.4 μL of denatured RCA reaction system (refer to Table 1) and subjected to RCA reaction at 30° C. for 30 minutes. After that, 5 μL of 0.5M EDTA as a stop solution was added to terminate the RCA reaction. All samples obtained were detected by using Qubit ssDNA Assay Kit (Q10212, INVITROGEN) for DNB concentration produced in the presence of the phi29 DNA polymerase mutant V470K-1474K, and the remaining activity ratio of enzyme was calculated.

Figure 3A:
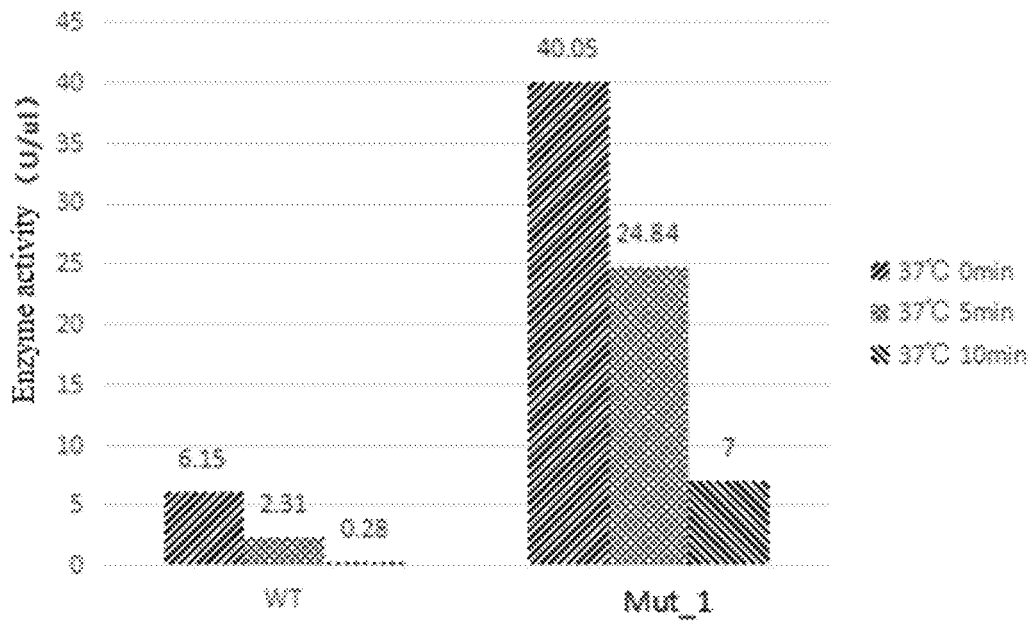
FIG. 3A and FIG. 3B show the detection results of pure wild-type phi29 DNA polymerase and phi29 DNA polymerase mutant V470K-1474K (Mut_1) for stability, where
Figure 3B:
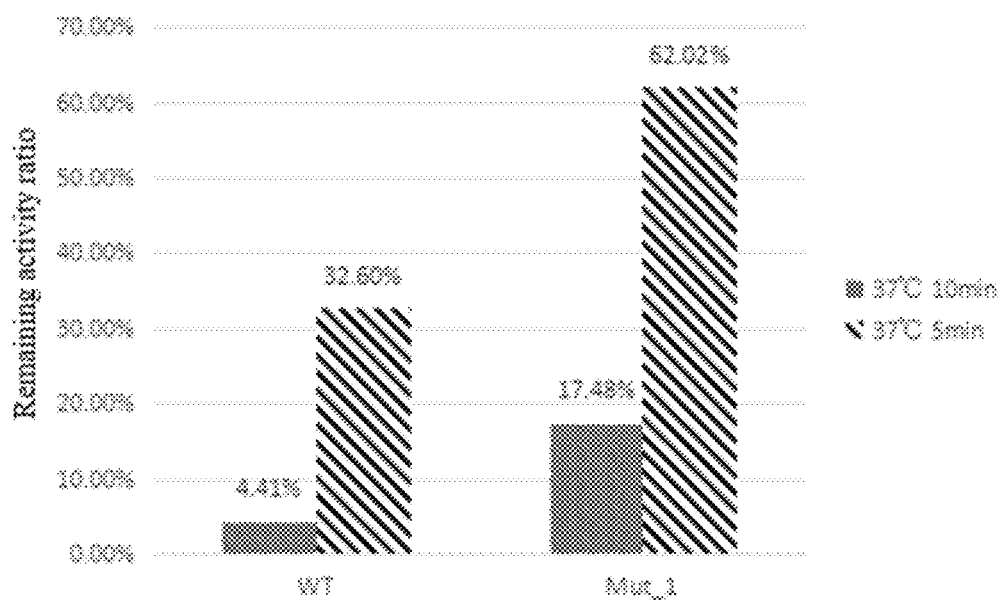

The results are shown in Table 4 and FIG. 3A and FIG. 3B. The phi29 DNA polymerase mutant V470K-474K (i.e. Mut_1) has a remaining activity ratio of 62.02% and 17.48% respectively, while the wild-type phi29 DNA polymerase has a remaining activity ratio of 37.56% and 4.55% respectively. The results demonstrate that the stability of phi29 DNA polymerase mutant V470K-474K is significantly higher than that of the wild-type phi29 DNA polymerase, which is also higher than that of phi29 DNA polymerase mutants V470K and I474K with a single-point mutation.

TABLE 4

Detection results of pure phi29 DNA polymerase mutant V470K-I474K for stability

| Polymerase type | Heat treatment temperature | Heat treatment time | Enzyme activity (U/μL) | Remaining activity ratio |
|---|---|---|---|---|
| WT | 37° C. | 0 min | 6.15 | N/A |
| | | 5 min | 2.31 | 37.56% |
| | | 10 min | 0.28 | 4.55% |
| V470K-I474K | 37° C. | 0 min | 40.05 | N/A |
| | | 5 min | 24.84 | 62.02% |
| | | 10 min | 7.00 | 17.48% |

INDUSTRIAL APPLICATION

The present disclosure has improved the stability of wild-type phi29 DNA polymerase through amino acid mutating, and a group of phi29 DNA polymerase mutants with increased stability have been obtained after screening. The present disclosure realizes to prepare and store the obtained phi29 DNA polymerase mutants under a reduced condition by mutating the amino acid sequence of wild-type phi29 DNA polymerase, which has reduced the production cost and the phi29 DNA polymerase mutants produced have prolonged validity period and improved efficiency.

What is claimed is:

1. A protein comprising amino acid mutations at positions 470 and 474 relative to the amino acid sequence of a wild-type phi29 DNA polymerase shown in SEQ ID NO: 2, wherein the protein has increased thermal stability compared to the wild-type phi29 DNA polymerase.

2. The protein according to claim 1, wherein the protein comprises
   a protein obtained by mutating valine at position 470 into lysine, isoleucine at position 474 into lysine and keeping remaining amino acids unchanged relative to the amino acid sequence of the wild-type phi29 DNA polymerase shown in SEQ ID NO: 2.

3. The protein according to claim 1, wherein the protein is a fusion protein obtained by ligating a tag at one or both of the N-terminus and the C-terminus of the protein.

4. A nucleic acid molecule encoding the protein as defined in claim 1.

5. A method for improving stability of a wild-type phi29 DNA polymerase comprising: mutating amino acids at positions 470 and 474 of the amino acid sequence of the wild-type phi29 DNA polymerase shown in SEQ ID NO: 2.

6. The method according to claim 5, wherein the stability is thermal stability.

* * * * *

SEQUENCE LISTING

```
<160> NUMBER OF SEQ ID NOS: 3

<210> SEQ ID NO 1
<211> LENGTH: 1728
<212> TYPE: DNA
<213> ORGANISM: Artificial Sequence
<220> FEATURE:
<223> OTHER INFORMATION: Nucleotide sequence encoding wild-type phi29
      DNA polymerase

<400> SEQUENCE: 1
atgaagcata tgccgcgcaa aatgtatagc tgcgactttg aaaccaccac caaagtggaa      60
gattgccgcg tttgggcgta tggctatatg aacatcgaag accacagcga atacaaaatt    120
ggcaacagcc tggatgaatt tatggcgtgg gtgctgaaag ttcaggcgga tctgtatttt    180
cacaacctga aatttgacgg cgcgttcatt attaactggc tggaacgcaa cggctttaaa    240
tggagcgcgg atggcttacc gaacaccttat aacaccatta ttagccgcat gggccagtgg    300
tatatgattg atatctgcct gggctataaa ggcaaacgca agattcatac cgtgatctat    360
gatagcctga gaaactgcc gtttccggtg aaaaaaatcg cgaaggactt taaactgacc    420
gtgctgaaag gcgatattga ctaccataaa gaacgcccgg tgggctataa aattaccccg    480
gaggaatatg cgtacatcaa gaacgacatc cagattattg cggaagcgct gctgattcag    540
tttaaacagg gcctggatcg tatgaccgcg ggtagcgata gcctgaaagg ctttaaggac    600
attatcacca ccaagaagtt caagaaagtg tttccgaccc tgagcctggg cctggataaa    660
gaagtgcgct atgcgtatcg cggtggcttt acctggctga cgatcgctt taaggaaaag    720 gaaattggcg aaggcatggt gtttgatgtg aacagcctgt atccggcgca gatgtatagc    780
cgcctgctgc cgtatggtga accgattgtg tttgaaggca gtatgtgtg ggatgaagat    840 tatccgctgc acattcagca tattcgctgc gaattcgaac tgaaggaagg ctatattccg    900
accattcaga ttaaacgcag ccgctttat aaaggcaacg agtacctgaa agcagcggc    960 ggcgaaattg cggatctgtg gctgagcaac gtggatctgg aactgatgaa agaacactac   1020
gatctgtaca acgtggaata tatcagcggc ctgaaattta agcgaccac cggcctgttt   1080 aaggactta tcgacaagtg gacctacatt aaaaccacca gcgaaggcgc gattaaacag   1140
ctggcgaaac tgatgctgaa cagcctgtat ggcaaatttg cgagcaaccc ggatgttacc   1200
ggcaaagtgc cgtatctgaa agaaaacggc gcgctgggct ttcgtttagg cgaagaggaa   1260
accaaagatc cggtgtatac cccgatgggc gtgtttatta ccgcgtgggc gcgctatacc   1320
accattaccg cggcgcaggc gtgttatgat cgcattatct attgcgatac cgatagcatt   1380
catctgaccg gcaccgaaat tccggatgtg atcaaagata ttgtggaccc gaaaaaactg   1440
ggctattggg cgcatgaaag cacctttaaa cgcgcgaaat atctgcgcca gaaaacctat   1500
atccaggaca tctacatgaa agaggtggat ggcaaactgg ttgaaggcag cccggatgat   1560
tataccgata ttaagttcag cgtgaaatgc gcgggcatga ccgataaaat taagaaggaa   1620
gtgaccttcg agaactttaa agtgggctt agccgcaaaa tgaaaccgaa accggttcag   1680
gtgcctggcg gtgttgttct ggtggatgat accttcacca tcaagtga              1728
```

-continued

<210> SEQ ID NO 2
<211> LENGTH: 575
<212> TYPE: PRT
<213> ORGANISM: Artificial Sequence
<220> FEATURE:
<223> OTHER INFORMATION: Amino acid sequence of wild-type phi29 DNA
      polymerase

<400> SEQUENCE: 2

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

```
Tyr Ile Lys Thr Thr Ser Glu Gly Ala Ile Lys Gln Leu Ala Lys Leu
    370             375             380

Met Leu Asn Ser Leu Tyr Gly Lys Phe Ala Ser Asn Pro Asp Val Thr
385             390             395             400

Gly Lys Val Pro Tyr Leu Lys Glu Asn Gly Ala Leu Gly Phe Arg Leu
            405             410             415

Gly Glu Glu Glu Thr Lys Asp Pro Val Tyr Thr Pro Met Gly Val Phe
            420             425             430

Ile Thr Ala Trp Ala Arg Tyr Thr Thr Ile Thr Ala Ala Gln Ala Cys
            435             440             445

Tyr Asp Arg Ile Ile Tyr Cys Asp Thr Asp Ser Ile His Leu Thr Gly
    450             455             460

Thr Glu Ile Pro Asp Val Ile Lys Asp Ile Val Asp Pro Lys Lys Leu
465             470             475             480

Gly Tyr Trp Ala His Glu Ser Thr Phe Lys Arg Ala Lys Tyr Leu Arg
            485             490             495

Gln Lys Thr Tyr Ile Gln Asp Ile Tyr Met Lys Glu Val Asp Gly Lys
            500             505             510

Leu Val Glu Gly Ser Pro Asp Asp Tyr Thr Asp Ile Lys Phe Ser Val
            515             520             525

Lys Cys Ala Gly Met Thr Asp Lys Ile Lys Lys Glu Val Thr Phe Glu
530             535             540

Asn Phe Lys Val Gly Phe Ser Arg Lys Met Lys Pro Lys Pro Val Gln
545             550             555             560

Val Pro Gly Gly Val Val Leu Val Asp Asp Thr Phe Thr Ile Lys
            565             570             575

<210> SEQ ID NO 3
<211> LENGTH: 25
<212> TYPE: DNA
<213> ORGANISM: Artificial Sequence
<220> FEATURE:
<223> OTHER INFORMATION: RCA Primer

<400> SEQUENCE: 3
tcttaagacc gcttggcctc cgact                                    25
```